US008461417B2

(12) United States Patent
Zou et al.

(10) Patent No.: US 8,461,417 B2
(45) Date of Patent: Jun. 11, 2013

(54) **REDUCTION OF *LYSO*-PHOSPHATIDYLCHOLINE ACYLTRANSFERASE ACTIVITY**

(75) Inventors: Jitao Zou, Saskatoon (CA); Qilin Chen, Saskatoon (CA); Wenyun Shen, Saskatchewan (CA); Liping Wang, Saskatchewan (CA)

(73) Assignee: National Research Council of Canada, Ottawa, ON (*) Notice: Subject to any disclaimer, the term of this patent is extended or adjusted under 35 U.S.C. 154(b) by 192 days.

(21) Appl. No.: 12/736,896

(22) PCT Filed: May 21, 2009

(86) PCT No.: PCT/CA2009/000712
§ 371 (c)(1),
(2), (4) Date: Nov. 19, 2010

(87) PCT Pub. No.: WO2009/140770
PCT Pub. Date: Nov. 26, 2009

(65) Prior Publication Data
US 2011/0088124 A1  Apr. 14, 2011

Related U.S. Application Data

(60) Provisional application No. 61/071,859, filed on May 21, 2008.

(51) Int. Cl.
*C12N 15/05* (2006.01)
*C12N 15/82* (2006.01)
*A01H 1/00* (2006.01)

(52) U.S. Cl.
USPC ........... 800/281; 800/278; 800/285; 800/286; 800/293; 800/294

(58) Field of Classification Search
None
See application file for complete search history.

(56) References Cited

U.S. PATENT DOCUMENTS

| | | | |
|---|---|---|---|
| 6,256,636 B1 | 7/2001 | Choy | |
| 6,500,670 B1 | 12/2002 | Zou et al. | |
| 7,015,373 B1 | 3/2006 | Zou et al. | |
| 7,112,724 B1 | 9/2006 | Zou et al. | |
| 7,214,856 B2 | 5/2007 | Umezawa et al. | |

FOREIGN PATENT DOCUMENTS

| | | |
|---|---|---|
| CA | 2517253 A1 | 9/2004 |
| WO | 2008076377 A2 | 6/2008 |
| WO | 2009001315 A2 | 12/2008 |

OTHER PUBLICATIONS

Alonso et al and supplement, 2003 Science 301, p. 653-657.*
Cahoon et al 2007, Current Opinions in Plant Biology 10: 236-244.*
Vrinten et al 2007, Biotechnology and Genetic Engineering Reviews 24: 263-280.*
Seedquest 2002, http://www.seedquest.com/News/releases/2002/february/4234.htm.*
SALK__004728C, 2006 TAIR, www.arabidopsis.org.*
SALK__105008, 2003 TAIR, www.arabidopsis.org.*
SALK__123480, 2002 TAIR, www.arabidopsis.org.*
Wang et al The Plant Cell Nov. 2012 vol. 24 No. 11 4652-4669.*
Alonso et al, 2003 Science 301, p. 653-657.*
Alvarez JP, Pekker I, Goldshmidt a, Blum E, Amsellem Z, Eshed Y (2006). Endogenous and synthetic microRNAs stimulate simultaneous, efficient, and localized regulation of multiple targets in diverse species. Plat Cell 18:1134-51.
Bechtold, N., Ellis, J. and Pellefer, G. (1993) In planta *Agrobacterium*-mediated gene transfer by infiltration of adult *Arabidopsis thaliana* plants. C.R. Acad. Sci. Ser. III Sci. Vie, 316: 1194-1199.
Becker, D., Brettschneider, R. and Lorz, H. (1994) Fertile transgenic wheat from microprojectile bombardment of scutellar tissue. Plant J. 5: 299-307.
Chen Q., Kazachkov M, Zheng Z, Zou J. (2007) The yeast acylglycerol acyltransferase LCA1 is a key component of Lands cycle for phosphatidylcholine turnover. FEBS Lett. Nov. 27;581(28):5511-6. Epub Nov. 8, 2007.
Datla, R, Anderson, J.W. and Selvaraj, G. (1997) Plant promoters for transgene expression. Biotechnology Annual Review 3: 269-296.
DeBlock, M., DeBrouwer, D. and Tenning, P. (1989) Transformation of *Brassica napus* and *Brassica oleracea* using *Agrobacterium tumefaciens* and the expression of the bar and neo genes in the transgenic platns. Plant Physiol. 91: 694-701.
Depicker A, Montagu MV (1997). Post-transcriptional gene silencing in plants. Curr Opin Cell Biol 9:373-82.
Helliwell CA, Waterhouse PM (2005). Constructs and methods for hairpin RNA-mediated gene silencing in plants. Methods Enzymology 392:24-35.
Henikoff S. Till BJ, Comai L (2004). Tilling. Traditional mutagenesis meets functional genomics. Plant Physiol 135:630-6.
Katavic,Y., Haughn, G.W., Reed, D., Martin, M. and Kunst, L. (1994) In planta transformation of *Arabidopsis thaliana*. Mol. Gen. Genet. 245:363-370.
Li X, Song Y, Century K, Straight S, Ronald P, Dong X, Lassner M, Zhang Y (2001). A fast neutron deletion mutagenesis-based reverse genetics system for plants. Plant J. 27:235-242.
Meyer, P. (1995) Understanding and controlling transgene expression. Trends in Biotechnology 13:332-337.
Miquel M and Browse J. (1992) *Arabidopsis* mutants deficient in polyunsaturated fatty acid synthesis. Biochemical and genetic characterization of a plant oleoyl-phosphatidylcholine desaturase. J Biol Chem. 267(3):1502-1509.
Moloney, M.M., Walker, J.M. and Sharma, K.K. (1989) High efficiency transformation of *Brassica napus* using *Agrobacterium* vectors. Plant Cell Rep. 8:238-242.

(Continued)

Primary Examiner — Brent T Page
Assistant Examiner — Matthew Keogh
(74) Attorney, Agent, or Firm — Laura Catherine Eckenswiller

(57) ABSTRACT

Reducing *lyso*-phosphatidylcholine acyltransferase (LPCAT) activity in a plant increases seed oil content and/or fatty acid levels in the plant. Increases in the level of unusual fatty acids 16:3, 18:3 and 20:1 c11 are particularly pronounced.

16 Claims, 4 Drawing Sheets

OTHER PUBLICATIONS

Nehra, N. S., Chibbar, R.N., Leung, N., Caswell, K., Mallard, C., Steinhauer, L. Baga, M. and Kartha, K.K. (1994) Self-fertile transgenic wheat platns regenerated from isolated. scutellar tissues following microprojectile bombardment with two distinct gene constructs. Plant J. 5:285-297.

Potrykus, L. (1991) Gene transfer to plants: Assessment of publish approaches and results. Annu. Rev. Plant Physiol. plant Mol. Biol. 42:205-225.

Rhodes, C.A., Pierce, D.A., mettler, I.J., Mascarenhas, D. and Detmer, J.J. (1988) Genetically transformed maize plants from protoplasts. Science 240: 204-207.

Sanford, J.C., Klein, T.M., Wolf, E.D. and Allen N. (1987) Delivery of substances into cells and tissues using a particle bombardment process. J. Part. Sci. Technol. 5: 27-37.

Schwab R, Ossowski S, Riester M, Warthmann N, Weigel D (2006). Highly specific gene silencing by artifical microRNAs in *Arabidopsis*. Plant Cell 18: 1121-33.

Shimamoto, K., Terada, R., Izawa, T. and Fujimoto, H. (1989) Fertile transgenic rice plants regenerated from transformed protoplasts. Nature 335: 274-276.

Songstad D.D., Somers, D.A. and Griesbach, R.J. (1995) Advances in alternative DNA delivery techniques. Plant Cell, Tissue and Organ Culture 40: 1-15.

Stam M, de Bruin R, van Blokland R, van der Hoom RA, Mol JN, Kooter JM (2000). Distinct features of post-transcriptional gene silencing by antisense transgenes in single copy and inverted T-DNA repeat loci. Plant J. 21:27-42.

Vasil, I.K. (1994) Molecular improvement of cereals. Plant Mol. Biol. 5:925-937.

Walden, R. and Wingender, R. (1995) Gene-transfer and plant regeneration techniques. Trends in Biotechnology 13: 324-331.

Shindou H and Shimizu T "Acyl-CoA:lysophospholipid acyltransferases" Journal of Biological Chemistry Jan. 2, 2009 284(1): 1-5 pISSN: 0021-9258; eISSN: 1083-351X.

Furukawa-Stoffer T et al. "Properties of lysophosphatidylcholine acyltransferase from *Brassica napus* cultures" Lipids Jun. 2003 38(6):651-656 pISSN:0024-4201; eISSN: 1558-9307.

Nakanishi H et al. "Cloning and characterization of mouse lung-type acyl-CoA:lysophosphatidylcholine acyltransferase 1 (LPCAT1)" Journal of Biological Chemistry Jul. 21, 2006 281(29):20140-20147 pISSN: oo21-9258; eISSN: 1083-351X.

Soupene E et al. "Mammalian acyl-CoA:lysophosphatidylcholine acyltransferase enzymes" Proceedings of the National Academy of Science USA Jan. 8, 2008 105(3):88-93 pISSN: 0027-8424; eISSN: 1091-6490.

Kazachkov M et al. "Substrate preferences of a lysophosphatidylcholine acyltransferase highlight its role in phospholipid remodeling" LIPIDS Electronic publication ahead of print: Sep. 10, 2008 43:895-902 pISSN: 0024-5201; eISSN: 1558-9307.

Ståhl U, Stålberg K, Stymne S, Ronne H., "A family of eukaryotic lysophospholipid acyltransferases with broad specificity", FEBS Lett. 2008 582:305-9.

ISR-Written-Opinion-on-PCT-CA2009-000712 dated Aug. 18, 2009.

* cited by examiner

REDUCTION OF LYSO-PHOSPHATIDYLCHOLINE ACYLTRANSFERASE ACTIVITY

CROSS-REFERENCE TO RELATED APPLICATIONS

This application is a national entry of International Patent Application PCT/CA2009/000712 filed May 21, 2009 and claims the benefit of United States Provisional Patent Application U.S. Ser. No. 61/071,859 filed May 21, 2008, the entire contents of both of which are herein incorporated by reference.

FIELD OF THE INVENTION

The present invention is related to biotechnology, in particular to methods of improving seed oil biosynthesis and accumulation of unusual fatty acids in a plant.

BACKGROUND OF THE INVENTION

Lyso-phosphatidylcholine (LPC) acyltransferase mediates the sn-2 acylation of LPC to produce phosphatidylcholine (PC). This enzyme represents a key component in the acyl group remodeling of phospholipid molecules. Active phospholipid remodeling may limit the accumulation of fatty acids into oil, and thus seed oil content, because the metabolic process of phospholipid deacylation and reacylation is considered a metabolic futile cycle. Acyl-remodeling is also implicated in the deposition of unusual fatty acids into storage lipids. Unusual fatty acid is a term used for fatty acid molecules that are not normally found in oilseed crops. Unusual fatty acids include hydroxyl fatty acids, very long chain fatty acids, short chain and medium short chain fatty acids, conjugated fatty acids, polyenoic fatty acids, epoxy fatty acids, acetylenic acids, etc. Because of a lack of understanding of acyl remodeling, efforts aimed at producing unusual fatty acids for industrial feedstock has met difficulty in reaching a level of commercial significance.

International Patent Application PCT/US2007/025650 filed Dec. 13, 2007 and U.S. patent application Ser. No. 11/820,014 filed Jun. 15, 2007 (Zou et al., 2007) disclose lyso-phosphatidylcholine acyltransferase (LPCAT) genes from yeast, plant and human. They further disclose that expression or over-expression of these genes in a cell modulates or enhances production of fatty acids, especially polyunsaturated fatty acids (PUFA) or other unusual fatty acids, and/or increases oil content in the cell. They further disclose a yeast mutant strain in which the gene, YOR175c, was knocked out thereby reducing LPCAT activity in the yeast. However, there is no report on the effect of reducing LPCAT activity on oil content and fatty acid levels.

Further, the function of the LPCAT gene in glycerolipid metabolism has been previously described (Chen 2007). However, this report did not describe the effect of reducing LPCAT activity on oil content and fatty acid levels.

SUMMARY OF THE INVENTION

It has now been surprisingly found that reducing lyso-phosphatidylcholine acyltransferase (LPCAT) activity increases overall oil content and increases rate of deposition of fatty acid, including unusual fatty acids, into oil, especially seed oil of a plant. Without being held to any particular mode of action, it is believed that reducing LPCAT activity reduces reacylation of fatty acid back to phospholipids and hence decreases the futile cycle of fatty acid group in and out of phospholipids.

Thus, there is provided a method of increasing seed oil content and/or fatty acid levels in a plant comprising reducing lyso-phosphatidylcholine acyltransferase (LPCAT) activity in the plant thereby increasing seed oil content and/or fatty acid levels in the plant in comparison to a control plant of the same species grown under the same conditions but not having LPCAT activity reduced therein.

There is further provided a method of increasing levels of unusual fatty acids in seed oil of a plant comprising reducing lyso-phosphatidylcholine acyltransferase (LPCAT) activity in the plant thereby increasing channeling of the unusual fatty acids into storage lipids in the plant in comparison to a control plant of the same species grown under the same conditions but not having LPCAT activity reduced therein.

There is yet further provided a plant comprising reduced lyso-phosphatidylcholine acyltransferase (LPCAT) activity and having increased seed oil content and/or fatty acid levels in comparison to a control plant of the same species grown under the same conditions but not having LPCAT activity reduced therein.

There is still yet further provided seed comprising increased seed oil content and/or fatty acid levels in comparison to seed from a control plant of the same species grown under the same conditions but not having LPCAT activity reduced therein, the seed being produced by a plant of the present invention.

Reducing LPCAT activity in a plant may be accomplished in a variety of ways, for example, by down-regulating or suppressing endogenous LPCAT gene expression in the plant and/or by generating plants comprising mutated LPCAT genes having lower activity than an endogenous LPCAT gene of the wild-type plant.

Down-regulation or silencing of LPCAT gene expression in plants may be accomplished by ways generally known in the art, for example, RNA interference (RNAi) techniques, artificial microRNA techniques, virus-induced gene silencing (VIGS) techniques, antisense techniques and sense co-suppression techniques. LPCAT gene mutations may be accomplished by ways generally known in the art, for example, targeted mutagenesis techniques.

RNAi techniques involve stable transformation using RNA interference (RNAi) plasmid constructs (Helliwell and Waterhouse, 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al, 2006; Alvarez et al, 2006). In this method, 21 nucleotide long fragments of the gene to be silenced are introduced into a pre-miRNA gene to form a pre-amiRNA construct. The pre-miRNA construct is transferred into the plant genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5 UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5 or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam et al., 2000.

Sense co-suppression techniques involve introducing a highly expressed sense transgene into a plant resulting in reduced expression of both the transgene and the endogenous gene (Depicker et al., 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to induce mutations in the gene and/or knockout the gene function in a plant (Henikoff, et al., 2004; Li et al., 2001). TILLING involves treating seeds or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression (e.g. silencing of the gene of interest). These plants may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in plant genomes that can also be detected using FOR in a manner similar to TILLING.

Preferred plants in which LPCAT activity may be reduced to increase seed oil content and/or fatty acid levels include crop species, especially oilseed plant species. Some examples include Brassicaceae spp. (e.g. rapeseed and Canola), *Borago* spp. (borage), *Ricinus* spp. (e.g. *Ricinus communis* (castor)), *Theobroma* spp. (e.g. *Theobroma cacao* (cocoa bean)), *Gossypium* spp. (cotton), *Crambe* spp., *Cuphea* spp., *Linum* spp. (flax), *Lesquerella* spp., *Limnanthes* spp., Linola, *Tropaeolum* spp. (nasturtium), *Olea* spp. (olive), *Elaeis* spp. (palm), *Arachis* spp. (peanut), *Carthamus* spp. (safflower), *Glycine* spp. (soybean), *Soja* spp. (soybean), *Helianthus* spp. (sunflower), *Vemonia* spp. Plants of particular note are from the family Brassicaceae, especially *Arabidopsis thaliana, Brassica napus, Brassica rapa, Brassica carinata, Brassica juncea*, and *Camelina sativa. Brassica* spp. and *Glycine* spp. are of particular note.

LPCAT genes and enzymes are known in the art, for example, as disclosed in enzyme class EC 2.3.1.23, and in Zou, J-T. et al., 2007 and Chen et al., 2007, the entire contents of which are herein incorporated by reference. The LPCAT gene from any particular species of plant may be identified by known techniques in the art, for example, by screening appropriate libraries that include the gene, wherein the screening is performed with the nucleotide sequence of a specific LPCAT gene known in the art or portions or probes thereof, or identified by sequence homology search using sequence alignment search programs such as BLAST, FASTA. As described previously, mutations or down-regulation of an LPCAT gene in a plant of interest can be accomplished in a variety of ways using sequence information of the LPCAT gene or one of its homologs.

Reducing LPCAT activity in a plant preferably increases overall seed oil content in the plant by 1 wt % or more based on the weight of the seed, more preferably by 2 wt % or more, in comparison to the seed oil content of the control plant.

Reducing LPCAT activity in a plant preferably increases overall levels of unusual fatty acids in the plant, particularly in seed oil of the plant, in comparison to the control plant. The increase in amount of unusual fatty acids is preferably 0.5 wt % or more based on the total weight of fatty acids, more preferably 1 wt % or more, even more preferably 2 wt % or more. Unusual fatty acids include, for example, hydroxyl fatty acids, very long chain fatty acids, short chain and medium short chain fatty acids, conjugated fatty acids, polyenoic fatty acids, epoxy fatty acids and acetylenic acids.

In certain embodiments, other methods of enhancing or altering oil production and/or fatty acid content in a plant may be used in conjunction with reducing LPCAT activity in the plant. For example, a nucleic acid sequence encoding another enzyme implicated in the production and/or modification of lipids and/or fatty acids may be incorporated into the plant. Such enzymes include, for example, fatty acid hydroxylase, fatty acyl-carrier protein (ACP) thioesterase, fatty acid elongase, fatty acid desaturase, fatty acid conjugase, fatty acid epoxygenase, fatty acid acetylenase, lysophophatidic acid acyltransferase, phospholipases, phospholipid diacylglycerol acyltransferase, *Brassica* pyruvate dehydrogenase kinase (see, e.g., U.S. Pat. No. 7,214,859 to Marilla et al. (May 8, 2007), U.S. Pat. No. 6,500,670 to Zou et al. (December 2002), and U.S. Pat. No. 6,256,636 to Randall et al. (July 2001), the contents of the entirety of each of which is incorporated herein by this reference), diacylglycerol acyltransferase (see, e.g., U.S. Pat. Nos. 7,015,373 and 6,500,670 to Zou et al. (December 2002), the contents of the entirety of each of which is incorporated herein by this reference), glycerol-3-phosphate dehydrogenase (see, e.g., U.S. Pat. No. 7,112,724, the contents of the entirety of which is incorporated herein by this reference), and combinations thereof.

Nucleic acid molecules that code for other enzymes implicated in the production and/or modification of lipids and/or fatty acids may be incorporated into the plant by a number of ways known in the art. For example, nucleic acid molecules and nucleic acid molecule constructs can be introduced into plants by a combination of transformation and tissue culture techniques that have been successfully integrated into effective strategies for creating transgenic plants. These methods, which can be used in the invention, have been described elsewhere (Potrykus, 1991; Vasil, 1994; Walden and Wingender, 1995; Songstad et al., 1995), and are well known to persons skilled in the art. For example, one skilled in the art will certainly be aware that, in addition to Agrobacterium mediated transformation of Arabidopsis by vacuum infiltration (Bechtold et at., 1993) or wound inoculation (Katavic et al., 1994), it is equally possible to transform other plant species, using Agrobacterium Ti-plasmid mediated transformation (e.g., hypocotyl (DeBlock et al., 1989) or cotyledonary petiole (Moloney et al., 1989) wound infection), particle bombardment/biolistic methods (Sanford et al., 1987; Nehra. et al., 1994; Becker et al., 1994) or polyethylene glycol-assisted, protoplast transformation (Rhodes et al., 1988; Shimamoto et al., 1989) methods.

As will also be apparent to persons skilled in the art, and as described elsewhere (Meyer, 1995; Dada et al., 1997), it is possible to utilize plant promoters to direct any intended regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock). Promoters for use herein may be inducible, constitutive, or tissue-specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

Promoter and termination regulatory regions that will be functional in the host plant cell may be heterologous (that is, not naturally occurring) or homologous (derived from the plant host species) to the plant cell and the gene. Suitable promoters which may be used are described above. The termination regulatory region may be derived from the 3' region of the gene from which the promoter was obtained or from another gene. Suitable termination regions which may be used are well known in the art and include Agrobacterium tumefaciens nopaline synthase terminator (Tnos), A. tumefaciens mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via Agrobacterium and screening for increased oil and/or fatty acid levels.

Suitably, the nucleotide sequences for the nucleic acid molecules that encode other enzymes may be extracted from, for instance, the GenBank® (a registered trademark of the U.S. Department of Health and Human Services) nucleotide database and searched for restriction enzymes that do not cut. These restriction sites may be added to the genes by conventional methods such as incorporating these sites in PCR primers or by sub-cloning.

Preferably, a nucleic acid molecule construct for use herein is comprised within a vector, most suitably an expression vector adapted for expression in an appropriate plant cell. It will be appreciated that any vector which is capable of producing a plant comprising the introduced nucleic acid sequence will be sufficient. Suitable vectors are well known to those skilled in the art and are described in general technical references such as Pouwels et al., Cloning Vectors. A Laboratory Manual, Elsevier, Amsterdam (1986). Particularly suitable vectors include the Ti plasmid vectors.

Transformation techniques for introducing the DNA constructs into host cells are well known in the art and include such methods as micro-injection, using polyethylene glycol, electroporation, or high velocity ballistic penetration. A preferred method relies on Agrobacterium-mediated transformation. After transformation of the plant cells or plant, those plant cells or plants into which the desired nucleic acid molecule has been incorporated may be selected by such methods as antibiotic resistance, herbicide resistance, tolerance to amino-acid analogues or using phenotypic markers. Various assays may be used to determine whether the plant cell shows an increase in gene expression, for example, Northern blotting or quantitative reverse transcriptase PCR (RT-FOR). Whole transgenic plants may be regenerated from the transformed cell by conventional methods.

Plants in which oil and/or unusual fatty acid production has been increased may be grown, their seeds harvested, and the oil and/or fatty acids of the seeds extracted by generally known techniques. The extracted oil and/or fatty acids may be used for subsequent incorporation into a composition, for example, a pharmaceutical composition, a nutraceutical composition or a food composition.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

All technical terms employed in this specification are commonly used in biochemistry, molecular biology and agriculture; hence, they are understood by those skilled in the field to which this invention belongs. Those technical terms can be found, for example in: *Molecular Cloning: A Laboratory Manual* 3rd ed., vol. 1-3, ed. Sambrook and Russell, Cold Spring Harbor Laboratory Press, Cold Spring Harbor, N.Y., 2001; *Current Protocols in Molecular Biology*, ed. Ausubel et al., Greene Publishing Associates and Wiley-Interscience, New York, 1988 (including periodic updates); *Short Protocols in Molecular Biology: A Compendium of Methods from Current Protocols in Molecular Biology* 5th ed., vol. 1-2, ed. Ausubel et al., John Wiley & Sons, Inc., 2002; *Genome Analysis: A Laboratory Manual*, vol. 1-2, ed. Green et al., Cold Spring Harbor Laboratory Press, Cold Spring Harbor, N.Y., 1997. Methodology involving plant biology techniques are described here and also are described in detail in treatises such as *Methods in Plant Molecular Biology: A Laboratory Course Manual*, ed. Maliga et al., Cold Spring Harbor Laboratory Press, Cold Spring Harbor, N.Y., 1995.

EXAMPLE 1

*Arabidopsis thaliana* Mutants

*A. thaliana* has two LPCAT genes denoted At1g63050 and At1g12640. Mutant lines 105008 and 004728c defective in At1g63050 and mutant line 123480 defective in At1g12640 were generated. Mutant line 105008 is reduced in the transcript At1g63050 but the transcript still exists therein. The At1g63050 transcript is completely absent from mutant line 004728c. The At1g12640 transcript is completely absent from mutant line 123480. These knockout lines were supplied by the ABRC stock center as line SALK_105008, SALK_004728C and SALK_123480. They were generated by T-DNA insertions in the *Arabidopsis* (Columbia ecotype) genome.

Figure 1:
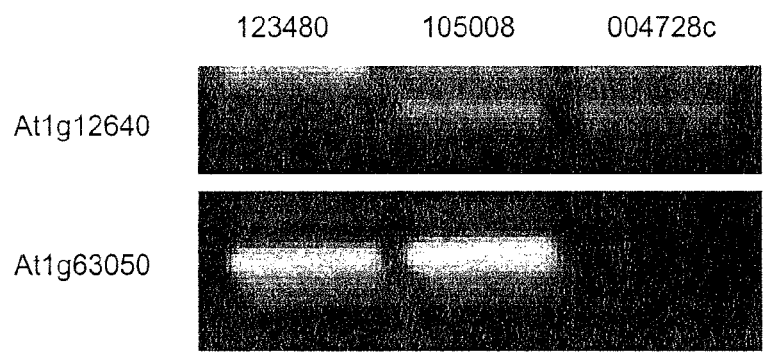
FIG. 1 depicts a RT-PCR experiment illustrating LPCAT gene expression in various Arabidopsis thaliana mutant lines. In line 123480, the expression of LPCAT1 (At1g12640) was not detectable, whereas in line 004728c, the expression of LPCAT2 (At1g63050) was absent.

Referring to FIG. 1, a RT-PCR experiment of LPCAT gene expression clearly shows that LPCAT gene expression was severely compromised in the 123480 and 004728c lines. Total RNA was extracted from *Arabidopsis* leaf tissues of various knockout lines with RNeasy Mini Kit (QIAGEN). First-strand cDNA was synthesized with SuperscriptII™ Synthesis Kit (Invitrogen). PCR reactions were performed with different gene specific primers.

EXAMPLE 2

Seed Oil Content in Knockout Mutants

Seed oil content in wild-type (WT) *A. thaliana* was compared to seed oil content in the *A. thaliana* knockout mutant line 004728c. Mutant line 004728c is a knockout mutant of At1g63050. Lines 004728c-1 and 004728c-2 are two independent lines grown under identical conditions along with the wild-type as control.

Oil content analysis was performed according to the following protocol. Dried seeds (about 5 mg) were weighed on an analytical balance and put into a glass tube (1 cm×10 cm) with Teflon™-lined screw cap was pre-rinsed thoroughly with chloroform and dried to remove any contaminating lipid residues. To this tube was added 1 ml of 5% (v/v) conc. sulfuric acid in MeOH (freshly prepared for each use), 25 µl of BHT solution (0.2% butylated hydroxy toluene in MeOH), 500 µg of 15:0 TAG (internal standard) and 300 µl of toluene as co-solvent. The mixture was vortexed for 30 s then heated at 90-95° C. for 1.5 h. After cooling to room temperature, 1.5 ml of 0.9% NaCl (w/v) was added and FAMEs were extracted with 3×2 ml hexane. Pooled extracts were evaporated under nitrogen and then dissolved in 400 µl of the hexane. The FAME extracts were analyzed by GC.

Figure 2:
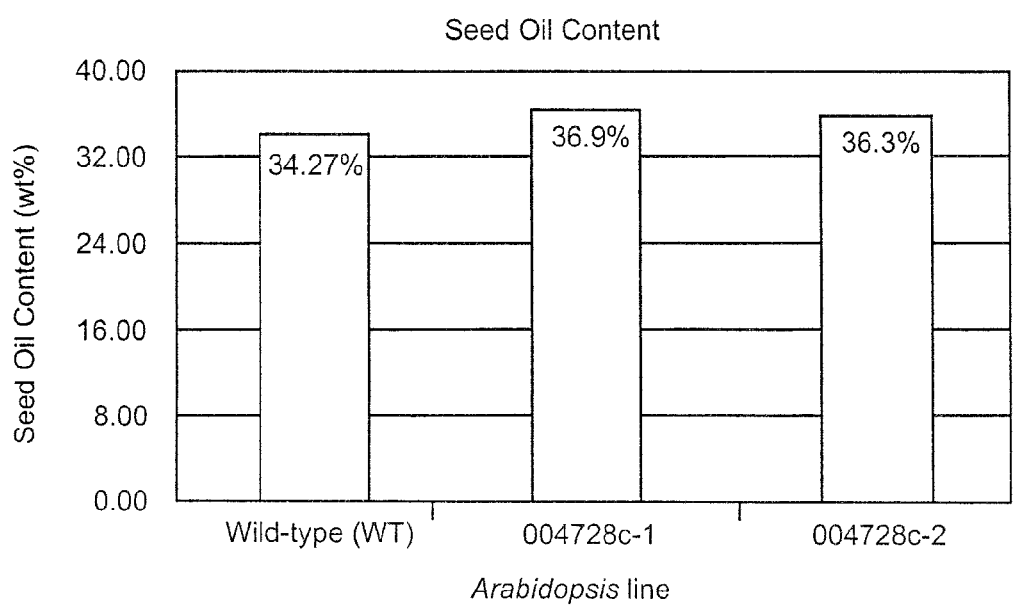
FIG. 2 depicts a graph comparing seed oil content in wild-type (WT) Arabidopsis thaliana to seed oil content in Arabidopsis thaliana LPCAT2 knockout mutant line 004728c.

Referring to FIG. 2, it is apparent that the seed oil content in the mutant line was significantly increased from about 34 wt % to about 36 wt % (i.e. by about 2 wt %) in comparison to the seed oil content of the wild-type plant.

EXAMPLE 3

Fatty Acid Composition in Knockout Mutants

Fatty acid composition in wild-type (WT) *A. thaliana* was compared to fatty acid composition in *A. thaliana* mutant lines. Fatty Acid and Lipid Analysis was performed according to the following protocol. Fatty acids in *Arabidopsis* were extracted with 2 ml of 10% KOH in methanol at 80° C. for 2 hr, followed by cooling and the addition of 1 ml of 50% HCl. Freed fatty acids were then extracted with 2 ml hexane, and dried under $N_2$. To each sample was then added 2 ml of 3 N methanol-HCl, followed by heating at 80° C. for 2 hr. After the addition of 2 ml of 0.9% NaCl solution and hexane, fatty acids were extracted into the organic phase and separated by GC. Lipids extraction and purification by two dimensional TLC on silica gel 60 (EMD chemical, Germany) was done according to the method of Miguel and Browse (1992). Lipids were visualized with iodine vapor. Individual lipids were isolated from TLC plates and used to prepare fatty acid methyl esters. The methyl esters were quantified by GC by using 17:0 fatty acid as internal standard.

Figure 3:
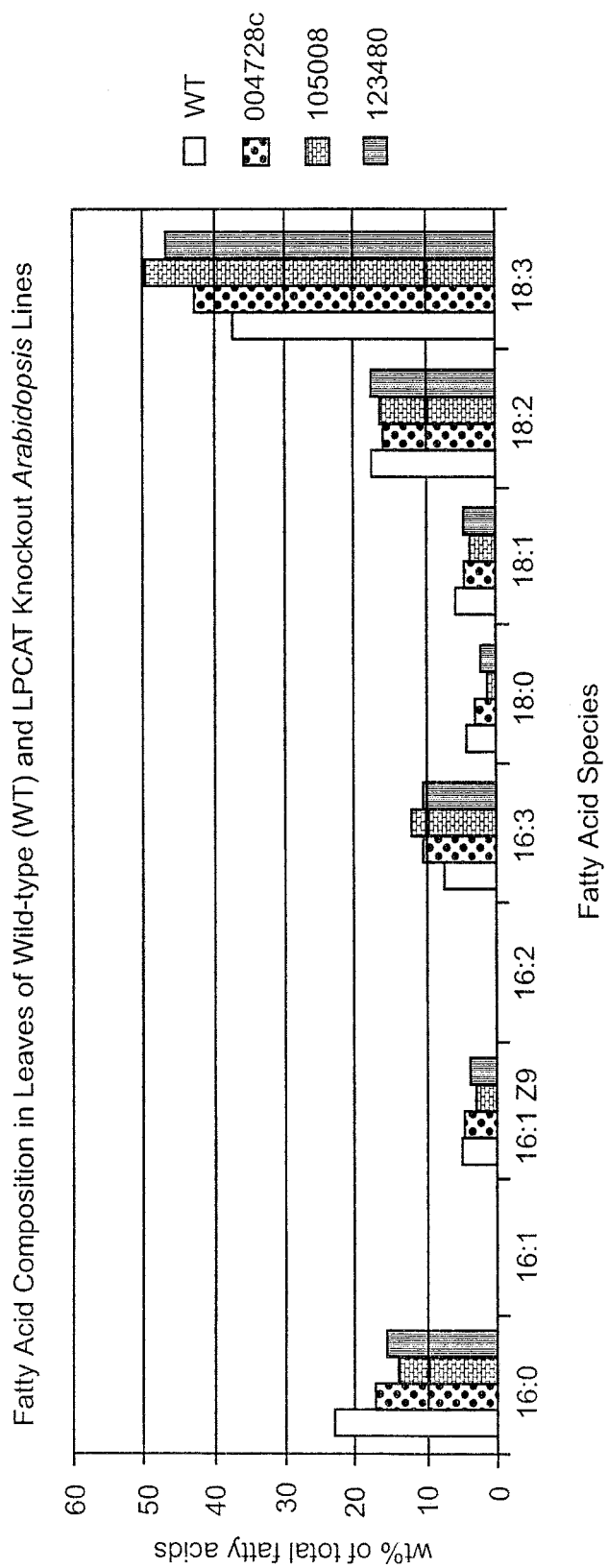
FIG. 3 depicts a graph comparing fatty acid composition (16:0, palmitic acid; 16:1, palmitoleic acid; 16:3, hexadecatrienoic acid; 18:0, stearic acid; 18:1, oleic acid; 18:2, linoleic acid; 18:3, lenolenic acid) in leaves of wild-type (WT) Arabidopsis thaliana to fatty acid composition in leaves of *Arabidopsis thaliana* LPCAT knockout mutant lines 004728c, 105008 and 123480.

Referring to FIG. 3, it is apparent that in leaves, there are clear and consistent changes in fatty acid profile in the glycerolipids. Notably, there is a significant increase in the amount of polyunsaturated fatty acids 16:3 and 18:3 (linolenic acid) in LPCAT defective mutant lines 004728c, 105008 and 123480 when compared to the amount of each in the wild-type plant. The amount of 16:3 fatty acid is increased in leaves by more than about 2 wt % based on the weight of all fatty acids. The amount of 18:3 fatty acid is increased in leaves by more than about 3 wt %, and as high as about 12 wt % in one mutant line, based on the weight of all fatty acids in the leaves. Lines 004728c and 105008 are progenies from a line defective in the LPCAT gene At1g63050, whereas line 123480 was from a mutant defective in a second LPCAT gene corresponding to At1g12640.

Figure 4:
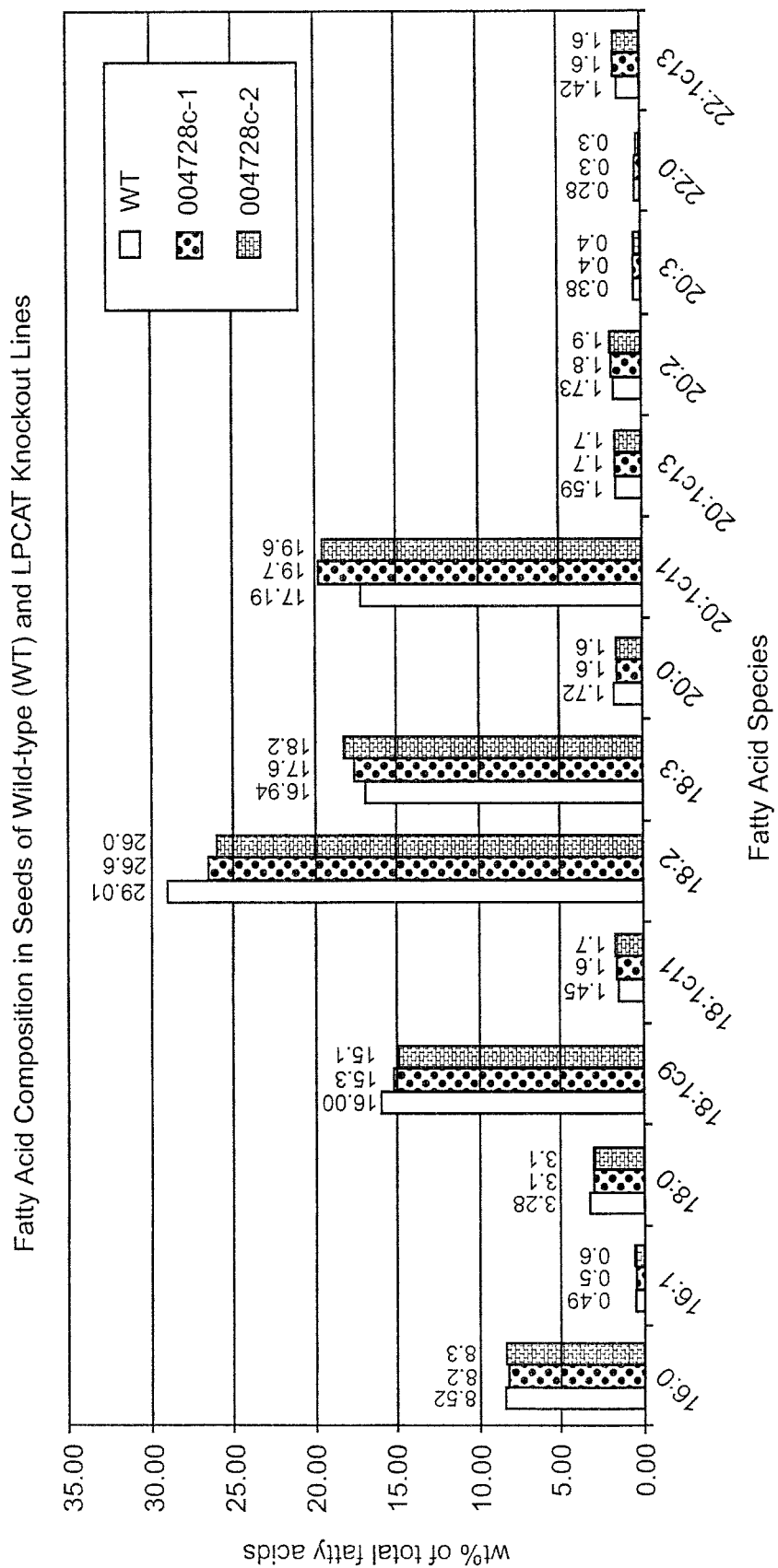
FIG. 4 depicts a graph comparing fatty acid composition (16:0, palmitic acid; 16:1, palmitoleic acid; 16:3, hexadecatrienoic acid; 18:0, stearic acid; 18:1, oleic acid; 18:2, linoleic acid; 18:3, lenolenic acid; 20:0, eicosanoic acid; 20:1 eicosenoic acid; 20:2 Eicosadienoic acid; 22:0 docosanoic acid; 22:1, erucic acid) in seeds of wild-type (WT) *Arabidopsis thaliana* to fatty acid composition in seeds of *Arabidopsis thaliana* LPCAT knockout mutant line 004728c.

Referring to FIG. 4, it is apparent that in seeds, there is a significant increase in the accumulation of unusual fatty acids, particularly the very long chain eicosenoic acid (20:1c11) and the polyunsaturated fatty acid linolenic acid (18:3) in mutant lines 004728c-1 and 004728c-2 as compared to the wild-type plant. There was also a slight increase in erucic acid (22:1c13) content. The amount of 18:3 fatty acid is increased in seeds by more than about 0.6 wt % based on the weight of all fatty acids. The amount of 20:1c11 fatty acid is increased in seeds by more than about 2.4 wt % based on the weight of all fatty acids in the seeds. In this experiment, about 4 mg of seeds was used for the analysis. Mutant line 004728c is a knockout mutant of At1g63050. Lines 004728c-1 and 004728c-2 are two independent lines grown under identical conditions along with the wild-type control.

EXAMPLE 4

Fatty Acid Composition in Over-expression Lines

For comparison, fatty acid compositional changes were studied in transgenic lines over-expressing the two *Arabidopsis* LPCAT genes LPCAT1 (At1g63050) and LPCAT2 (At1g12640). The genes were transformed into wild type *Arabidopsis* plants using standard protocols under the transcriptional control of a constitutive promoter (35S).

Figure 5A:
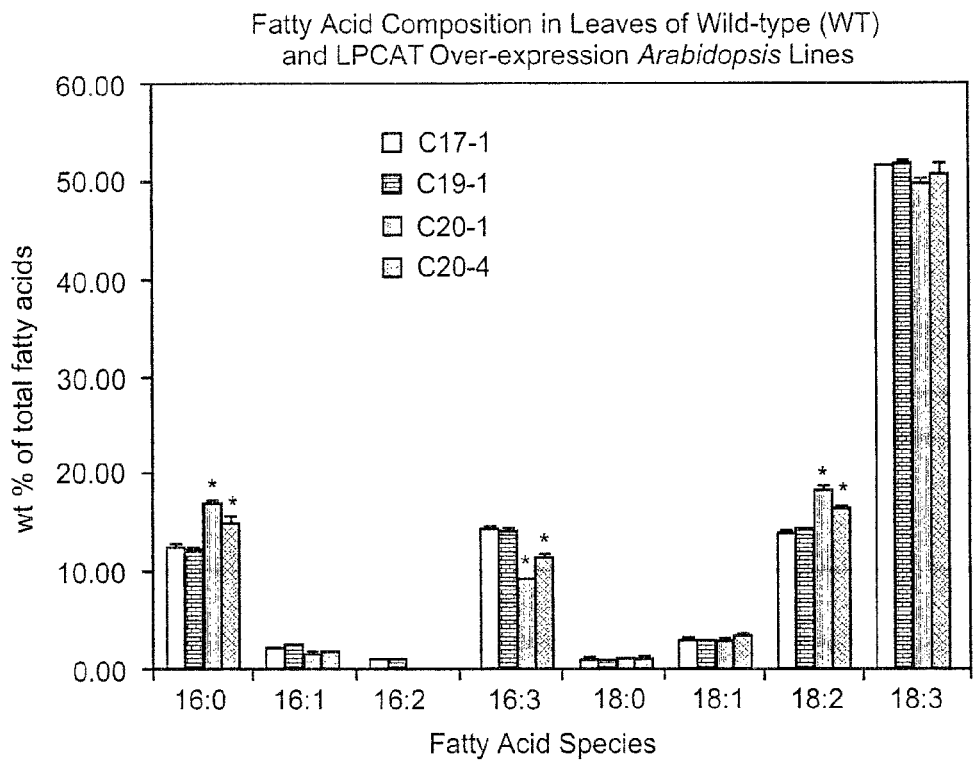
FIG. 5 depicts graphs of fatty acid composition in leaves (FIG. 5A) and seeds (FIG. 5B) of *Arabidopsis thaliana* wild type plants transformed with LPCAT1 or LPCAT2 gene for over-expression of LPCAT. C17-1 is control vector; C19-1 is 35S::LPCAT1; C20-1 is 35S::LPCAT2 (weak phenotype); C20-4 is 35S::LPCAT2 (strong phenotype).
Figure 5B:
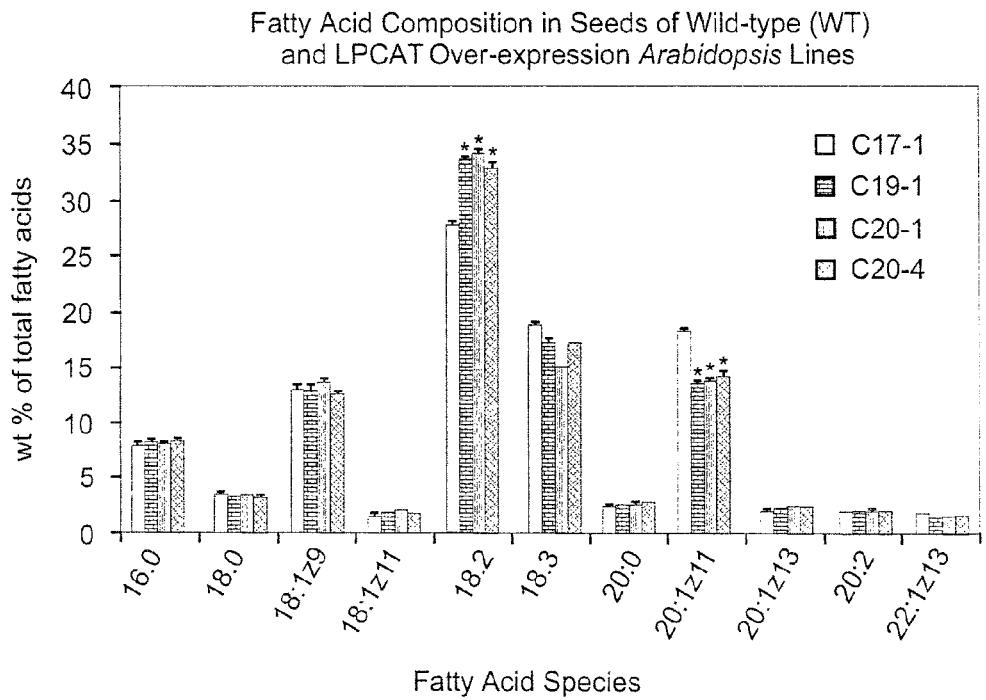

Referring to FIG. 5A, in leaf tissues of the transgenic lines, over-expression of LPCAT1 (line 019-1) had no impact on glycerolipid fatty acid composition; but over expression of LPCAT2 (C20-1, C20-4) resulted in increases of 16:0 and 18:0 fatty acids, and reduced 16:3 and 18:3, respectively. Referring to FIG. 5B, in the seed oil, both LPCAT1 and LPCAT2 over-expression led to a reduced very long chain fatty acid (20:1) content. This result is opposite that of the LPCAT knockout mutants described in the previous examples (e.g. LPCAT knockout lines had higher 20:1 content).

References: The contents of the entirety of each of which are incorporated by this reference.

Alvarez J P, Pekker I, Goldshmidt A, Blum E, Amsellem Z, Eshed Y (2006). Endogenous and synthetic microRNAs stimulate simultaneous, efficient, and localized regulation of multiple targets in diverse species. *Plant Cell* 18:1134-51.

Ausubel et al. ed. (2002) *Current Protocols in Molecular Biology*, Greene Publishing Associates and Wiley-Interscience, New York, 1988 (including periodic updates).

Ausubel et al. ed. (2002) *Short Protocols in Molecular Biology: A Compendium of Methods from Current Protocols in Molecular Biology* 5th ed., vol. 1-2, ed. John Wiley & Sons, Inc.

Bechtold, N., Ellis, J. and Pellefer, G. (1993) In planta *Agrobacterium*-mediated gene transfer by infiltration of adult *Arabidopsis thaliana* plants. *C.R. Acad. Sci. Ser. III Sci. Vie*, 316: 1194-1199.

Becker, D., Brettschneider, R. and Lorz, H. (1994) Fertile transgenic wheat from microprojectile bombardment of scutellar tissue. *Plant J.* 5: 299-307.

Chen Q, Kazachkov M, Zheng Z, Zou J. (2007) The yeast acyiglycerol acyltransferase LCA1 is a key component of Lands cycle for phosphatidylcholine turnover. *FEBS Lett.* November 27; 581(28):5511-6. Epub 2007 Nov. 8.

Datla, R, Anderson, J. W. and Selvaraj, G. (1997) Plant promoters for transgene expression. *Biotechnology Annual Review* 3: 269-296.

DeBlock, M., DeBrouwer, D. and Tenning, P. (1989) Transformation of *Brassica napus* and *Brassica oleracea* using *Agrobacterium tumefaciens* and the expression of the bar and neo genes in the transgenic plants. *Plant Physiol.* 91: 694-701.

Depicker A, Montagu M V (1997). Post-transcriptional gene silencing in plants. *Curr Opin Cell Biol* 9:373-82.

Green et al. ed. (1997) *Genome Analysis: A Laboratory Manual*, vol. 1-2, Cold Spring Harbor Laboratory Press, Cold Spring Harbor, N.Y.

Helliwell C A, Waterhouse P M (2005). Constructs and methods for hairpin RNA-mediated gene silencing in plants. *Methods Enzymology* 392:24-35.

Henikoff S, Till B J, Comai L (2004). TILLING. Traditional mutagenesis meets functional genomics. *Plant Physiol* 135:630-6.

Katavic, Y., Haughn, G. W., Reed, D., Martin, M. and Kunst, L. (1994) In planta transformation of *Arabidopsis thaliana*. *Mol. Gen. Genet.* 245: 363-370.

Li X, Song Y, Century K, Straight S, Ronald P, Dong X, Lassner M, Zhang Y (2001). A fast neutron deletion mutagenesis-based reverse genetics system for plants. *Plant J.* 27:235-242.

Maliga et al. (1995) *Methods in Plant Molecular Biology: A Laboratory Course Manual*, Cold Spring Harbor Laboratory Press, Cold Spring Harbor, N.Y.

Meyer, P. (1995) Understanding and controlling transgene expression. *Trends in Biotechnology* 13: 332-337.

Miguel M and Browse J. (1992) *Arabidopsis* mutants deficient in polyunsaturated fatty acid synthesis. Biochemical and genetic characterization of a plant oleoyl-phosphatidylcholine desaturase. *J Biol Chem.* 267(3):1502-1509.

Moloney, M. M., Walker, J. M. and. Sharma, K. K. (1989) High efficiency transformation of *Brassica napus* using *Agrobacterium* vectors. *Plant Cell Rep.* 8: 238-242.

Nehra, N. S., Chibbar, R. N., Leung, N., Caswell, K., Mallard, C., Steinhauer, L. Baga, M. and Kartha, K. K. (1994) Self-fertile transgenic wheat plants regenerated from isolated. scutellar tissues following microprojectile bombardment with two distinct gene constructs. *Plant J.* 5: 285-297.

Potrykus, L. (1991) Gene transfer to plants: Assessment of publish approaches and results. *Annu. Rev. Plant Physiol. Plant Mol. Biol.* 42: 205-225.

Pouwels et al., (1986) *Cloning Vectors*. A laboratory manual, Elsevier, Amsterdam.

Rhodes, C. A., Pierce, D. A., Mettler, I. J., Mascarenhas, D. and Detmer, J. J. (1988) Genetically transformed maize plants from protoplasts. *Science* 240: 204-207.

Sambrook and Russell ed., (2001) *Molecular Cloning: A Laboratory Manual* 3rd ed., vol. 1-3, Cold Spring Harbor Laboratory Press, Cold Spring Harbor, N.Y.

Sanford, J. C., Klein, T. M., Wolf, E. D. and Allen, N. (1987) Delivery of substances into cells and tissues using a particle bombardment process. *J. Part. Sci. Technol.* 5: 27-37.

Schwab R, Ossowski S, Riester M, Warthmann N, Weigel D (2006). Highly specific gene silencing by artificial microRNAs in *Arabidopsis*. *Plant Cell* 18:1121-33.

Shimamoto, K., Terada, R., Izawa, T. and Fujimoto, H. (1989) Fertile transgenic rice plants regenerated from transformed protoplasts. *Nature* 335: 274-276.

Songstad D. D., Somers, D. A. and. Griesbach, R. J. (1995) Advances in alternative DNA delivery techniques. *Plant Cell, Tissue and Organ Culture* 40: 1-15.

Stam M, de Bruin R, van Blokland R, van der Hoorn R A, Mol J N, Kooter J M (2000). Distinct features of post-transcriptional gene silencing by antisense transgenes in single copy and inverted T-DNA repeat loci. *Plant J.* 21:27-42.

Vasil, I. K. (1994) Molecular improvement of cereals. *Plant Mol. Biol.* 5: 925-937.

Walden, R. and Wingender, R. (1995) Gene-transfer and plant regeneration techniques. *Trends in Biotechnology* 13: 324-331.

Zou, J-T. et al. (2007). "Genes Encoding a Novel Type of Lysophophatidylcholine Acyltransferases and Their Use to Increase Triacylglycerol Production and/or Modify Fatty Acid Composition", International Patent Application PCT/US2007/025650 filed Dec. 13, 2007 and U.S. patent application Ser. No. 11/820,014 filed Jun. 15, 2007.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of increasing seed oil content and/or fatty acid levels in an *Arabidopsis thaliana* plant comprising down-regulating either At1g12640 or At1g63050, suppressing endogenous At1g12640 or At1g63050 gene expression, or generating a plant comprising either a mutated At1g12640 or a mutated At1g63050 gene thereby reducing lyso-phosphatidylcholine acyltransferase (LPCAT) activity in the plant thereby increasing seed oil content and/or fatty acid levels in the plant in comparison to a control plant of the same species grown under the same conditions but not having LPCAT activity reduced therein, and determining that seed oil content and/or fatty acid levels in the plant have increased.

2. The method according to claim 1, wherein the seed oil content is increased by 1 wt % or more based on the weight of the seed.

3. The method according to claim 1, wherein the seed oil content is increased by 2 wt % or more based on the weight of the seed.

4. A method of increasing levels of 20:1 c11 fatty acids in seed oil of a plant comprising down-regulating or suppressing endogenous LPCAT gene expression in the plant and/or generating a plant comprising a mutated LPCAT gene having lower activity than an endogenous LPCAT gene of the plant to thereby reduce lyso-phosphatidylcholine acyltransferase (LPCAT) activity in the plant thereby increasing channeling of 20:1 c11 fatty acids into storage lipids in the plant in comparison to a control plant of the same species grown under the same conditions but not having LPCAT activity reduced therein, and determining that levels of 20:11c11 fatty acids have increased in the seed oil.

5. The method according to claim 1, wherein 20:1c11 fatty acid, 16:3 fatty acid and/or 18:3 fatty acid levels are increased in comparison to the amount of each in the control plant.

6. The method according to claim 5, wherein, the 20:1c11, 18:3 and 16:3 fatty acids are each increased by 0.5 wt % or more based on the total weight of fatty acids.

7. The method according to claim 1, wherein 20:1c11 fatty acid levels in seed is increased by more than 2.4 wt % based on the weight of all fatty acids in the seed.

8. The method according to claim 1, wherein a nucleic acid sequence encoding another enzyme implicated in production and/or modification of lipids and/or fatty acids is incorporated into the plant.

9. The method according to claim 8, wherein the other enzyme is a fatty acid hydroxylase, a fatty acyl-carrier protein (ACP) thioesterase, a fatty acid elongase, a fatty acid desaturase, a fatty acid conjugase, a fatty acid epoxygenase, a fatty acid acetylenase, a lysophosphatidic acid acyltransferase, a phospholipase, a phospholipid diacylglycerol acyltransferase, a *Brassica* pyruvate dehydrogenase kinase, a diacylglycerol acyltransferase, a glycerol-3-phosphate dehydrogenase or combinations thereof.

10. The method according to claim 4, wherein, the 20:1 c11 fatty acids are increased by 0.5 wt % or more based on the total weight of fatty acids.

11. The method according to claim 4, wherein 20:1 c11 fatty acid levels in the seed are increased by more than 2.4 wt % based on the weight of all fatty acids in the seed.

12. The method according to claim 4, wherein the plant is from *Brassica* spp., *Borago* spp, *Ricinus* spp., *Theobroma* spp., *Gossypium* spp., *Crambe* spp., *Cuphea* spp., *Linum* spp., *Lesquerella* spp., *Limnanthes* spp., *Linola*, *Tropaeolum* spp., *Olea* spp., *Elaeis* spp., *Arachis* spp., *Carthamus* spp., *Glycine* spp., *Soja* spp., *Helianthus* spp. or *Vernonia* spp.

13. The method according to claim 4, wherein the plant is from the family *Brassicaceae*.

14. The method according to claim 4, wherein the plant is from *Brassica* spp. or *Glycine* spp.

15. The method according to claim 4, wherein a nucleic acid sequence encoding another enzyme implicated in production and/or modification of lipids and/or fatty acids is incorporated into the plant.

16. The method according to claim 15, wherein the other enzyme is a fatty acid hydroxylase, a fatty acyl-carrier protein (ACP) thioesterase, a fatty acid elongase, a fatty acid desaturase, a fatty acid conjugase, a fatty acid epoxygenase, a fatty acid acetylenase, a lysophosphatidic acid acyltransferase, a phospholipase, a phospholipid diacylglycerol acyltransferase, a *Brassica* pyruvate dehydrogenase kinase, a diacylglycerol acyltransferase, a glycerol-3-phosphate dehydrogenase or combinations thereof.

* * * * *